(12) United States Patent
Sazy

(10) Patent No.: US 6,648,915 B2
(45) Date of Patent: *Nov. 18, 2003

(54) INTERVERTEBRAL CAGE AND METHOD OF USE

(76) Inventor: John A. Sazy, 3217 Omega Dr., Arlington, TX (US) 76014

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/471,312

(22) Filed: Dec. 23, 1999

(65) Prior Publication Data

US 2002/0055781 A1 May 9, 2002

(51) Int. Cl.$^7$ .................................................. A61F 2/44
(52) U.S. Cl. ..................................... 623/17.11; 623/902
(58) Field of Search ......................... 623/17.11, 17.16, 623/23.53, 23.54, 23.63, 908, 902; 606/61

(56) References Cited

U.S. PATENT DOCUMENTS

| | | | | |
|---|---|---|---|---|
| 3,867,728 A | * | 2/1975 | Stubstad et al. | 623/17.16 |
| 4,820,305 A | * | 4/1989 | Harms et al. | 623/16.11 |
| 5,609,637 A | * | 3/1997 | Biedermann et al. | 623/17.16 |
| 5,665,122 A | | 9/1997 | Kambin | 623/17 |
| 5,702,449 A | * | 12/1997 | McKay | 623/17.16 |
| 5,800,550 A | | 9/1998 | Sertich | 623/17 |
| 5,827,289 A | * | 10/1998 | Reiley et al. | 606/86 |
| 5,941,880 A | | 8/1999 | Errico et al. | 606/61 |
| 6,086,613 A | * | 7/2000 | Camino et al. | 623/17.16 |
| 6,143,032 A | * | 11/2000 | Schafer et al. | 623/17.11 |
| 2002/0019637 A1 | * | 2/2002 | Frey et al. | 606/85 |

* cited by examiner

Primary Examiner—Bruce Snow
Assistant Examiner—Brian E Pellegrino
(74) Attorney, Agent, or Firm—Charles D. Gunter, Jr.

(57) ABSTRACT

An intervertebral prosthesis for implantation between adjacent vertebrae of the human spine is shown. The prosthesis is formed as a unitary cage body configured and sized to be inserted between adjacent vertebrae in a single step implantation procedure. The cage body is banana shaped as viewed from above, the body having an exterior surface and an interior surface, the interior surface defining an internal recess for receiving cancellous bone material during an implantation procedure. The cage body can be formed as an interlinked mesh.

5 Claims, 6 Drawing Sheets

INTERVERTEBRAL CAGE AND METHOD OF USE

BACKGROUND OF THE INVENTION

1. Field of the Invention

The present invention relates generally to a human spinal implant device for implantation into intervertebral space between adjacent vertebral bones and to a surgical method for installing such a spinal implant assembly.

2. Description of the Prior Art

Genetic or developmental irregularities, trauma, chronic stress, tumors, and degenerative wear are typical causes which can result in spinal pathologies for which surgical intervention is necessary. Various devices and techniques are disclosed in the prior art for immobilizing and/or fusing adjacent bones by implanting artificial devices in or on the spinal column. The region of the back which needs to be immobilized, as well as the individual variations in anatomy, determine the appropriate surgical protocol and implantation device which is best suited for the case at hand. Where a failure of the intervertebral disc is concerned, the inter-body fusion implant is often chosen.

An inter-body fusion maintains disc height, helps to protect the nerve root and restores weight-bearing ability to anterior structures. The fusion also restores the annular region of the spine to tension and immobilizes the unstable, degenerated intervertebral disc. Anterior approaches and fusion in the cervical region have gained wide acceptance by both neurosurgeons and orthopedic surgeons as treatment for herniated discs, trauma and related degenerative conditions. In the case of lower lumbar spine problems, such techniques have had more sporadic success. Recently, pedicel screws and rods have allowed surgeons to reduce degenerative conditions and immobilize the motion segment, but have not eliminated the need for weight-bearing support for the anterior spinal column.

The prior art implant techniques have generally involved two component implant assemblies. The surgical procedures for installing such devices can be complicated and traumatic to the patient. Although X-ray imaging can be used to determine the approximate location of the respective two component assemblies, alignment of the prostheses can obviously be of major concern.

Accordingly, it is an object of the present invention to provide a new and improved single component inter-body fusion cage which overcomes known deficiencies of the prior art while providing improved overall results.

SUMMARY OF THE INVENTION

The apparatus of the invention is an intervertebral prosthesis for implantation between adjacent vertebrae of the human spinal column. The prosthesis comprises a unitary body configured and sized to be inserted between adjacent vertebrae in a single step implantation procedure. The body is banana-shaped as viewed from above and has an exterior surface and an interior surface, the interior surface defining an internal recess for receiving cancellous bone material during an implantation procedure. Preferably, the unitary body is a cage which is formed as interlinked mesh. Most preferably, the banana-shaped cage body is a ring of metal having evenly spaced openings about a circumference of the body. The preferred cage body is formed of a hard metal alloy, such as a titanium alloy. The intervertebral prosthesis is selectively sized to fit within a vertebral disk space of a human anatomy allowing adequate space for additional cancellous bone anterior to the cage body within the disk space.

The method of the invention facilitates inter-body fusion in the vertebral column by providing an improved prosthesis and method of installation. A space is first prepared for receiving a prosthetic device between two vertebrae. The banana-shaped spinal cage body is then surgically inserted into the space between the vertebrae. The banana-shaped cage body has an exterior surface and an interior surface, the interior surface defining an internal recess for receiving cancellous bone material during an implantation procedure. Preferably, the cage body is a ring of metal having evenly spaced openings about a circumference of the body. The cage body forms an interlinked mesh. The preferred cage body is formed of a hard metal alloy. Preferably, the cage body is formed of a titanium alloy.

Additional objects, features and advantages will be apparent in the written description which follows.

DESCRIPTION OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs.

Figure 1:
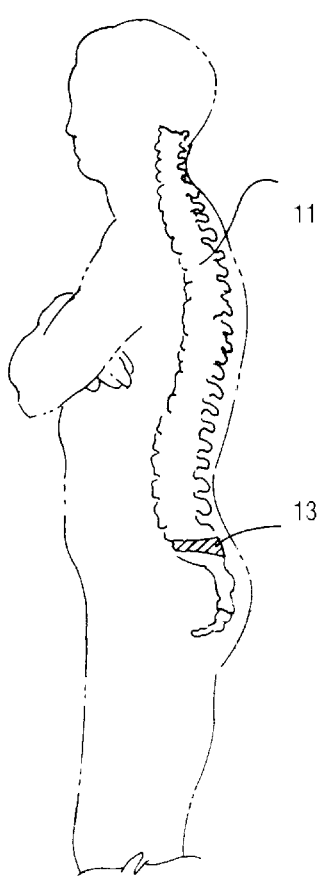
FIG. 1 is a simplified side view of the human anatomy, showing the spinal process.

These more than 20 bones are anatomically referred to as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae and connect to the lower spine comprising the 5 lumbar vertebrae. The base of the spine is the sacral bones. The component bones of the cervical spine are generally smaller than those of the thoracic spine, which are in turn smaller than those of the lumbar region. The sacral region connects laterally to the pelvis. FIG. 1 is a simplified schematic of the human anatomy showing the spinal column 11 and intervertebral disc space 13 which, in this case, is at approximately the L4–L5 location.

The spinal column of bones is highly complex, serving to house and protect critical elements of the nervous system having countless peripheral nerves and circulatory bodies in close proximity. Surgical procedures are therefore delicate and demanding by their very nature. In the case of spinal pathologies for which surgical intervention is necessary, particularly with respect to failure of the intervertebral disc, the interbody fusion implant has found acceptance in the field because such devices can be implanted into the anterior of the spine and maintain disc height, protect the nerve root and restore weight bearing ability to the anterior structures. Typically a pair of elements were implanted. The elements themselves were sometimes cylindrical or tubular bodies, solid plugs or cage designs, to mention a few. The present invention is directed to an improved unitary cage and method for its installation.

Figure 2:
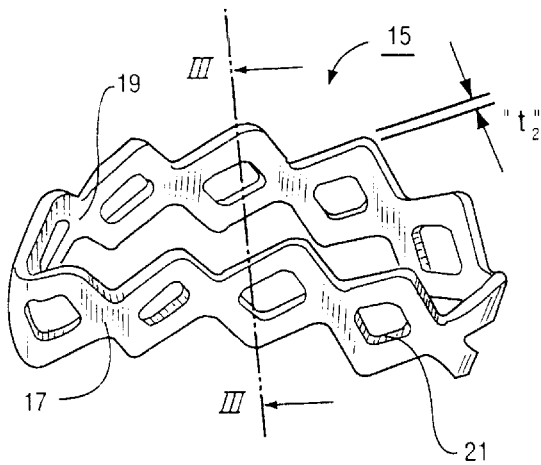
FIG. 2 is a close up, perspective view of the spinal implant of the invention.
Figure 4:
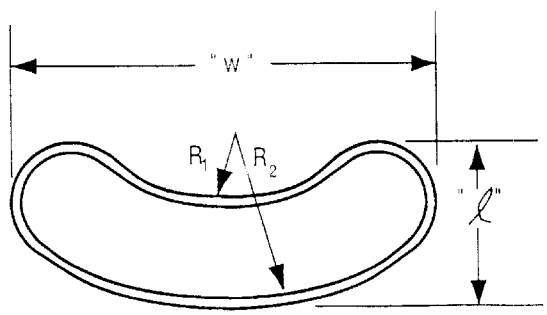
FIG. 4 is a top view of the banana-shaped device of the invention showing certain of the dimensions thereof.

FIG. 2 shows the implant device of the invention, designated generally as 15. In the preferred embodiment illustrated, the unitary body 15 is a cage configured and sized to be inserted between adjacent vertebrae in a single step implantation procedure. As shown in FIGS. 2 and 4, the cage 15 is "banana-shaped" as view from above. The body has an exterior surface 17 and an interior surface 19. The interior surface 19 defines an internal recess or enclosure for receiving cancellous bone material during an implantation procedure. The preferred cage body, as best seen in FIG. 2, is a ring having evenly spaced openings 21 about a circumference of the body. The double bands form a serpentine arrangement which comprises an interlinked mesh in the preferred embodiment shown in FIG. 2.

A preferred material for the cage body 15 is a hard metal alloy, preferably titanium or stainless steel. Other preferred materials include carbon fiber, bioreabsorbable materials such as polyglycotic acid, polylactic acid and other synthetic materials such as polymethylmethacrylate PMMA blended with various antibiotic admixtures for the treatment of discitis and vertebral osteomyelitis.

Figure 3:
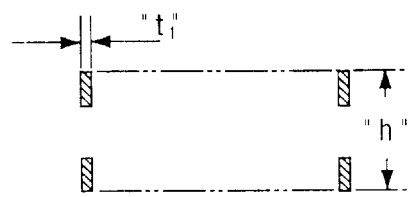
FIG. 3 is a cross sectional view of the spinal implant of FIG. 2, taken along line II—II, and illustrating the cross-sectional thickness of the device of the invention.

The cage body is selectively sized to fit within a vertebral disc space of a human anatomy allowing adequate space for additional cancellous bone anterior to the cage body within the disc space. Referring to FIGS. 3 and 4, the cage 15 is typically provided in a range of widths "w" of 24 mm, 26 mm and 28 mm. The lengths "1" are typically 8 mm, 9 mm and 10 mm. The heights are 10 mm, 12 mm, 14 mm and 16 mm. The thickness of the titanium "t1" is approximately 1.5 mm. The thickness of the mesh material "t2" is approximately 2 mm. The radius of curvature "R1" of the front arc of the cage is approximately 1.5 mm. The radius of curvature "R2" of the posterior or back arc of the cage is approximately 1.5 mm.

The unitary cage 15 can be placed from an anterior position (anterior interbody fusion or ALIF), or posteriorly (posterior lumbar interbody fusion or PLIF, transforaminal interbody fusion or TLIF). The cage is curved so that it mirrors the natural radius or curvature of the anterior and posterior curves of the vertebral bodies. It can be placed from an anterior position or posterolateral position after standard discectomy.

Figure 5:
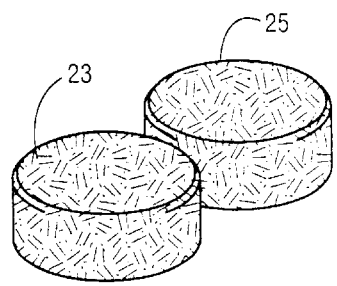
FIG. 5 is a perspective view of two of the prior art devices used as spinal prostheses.
Figure 6:
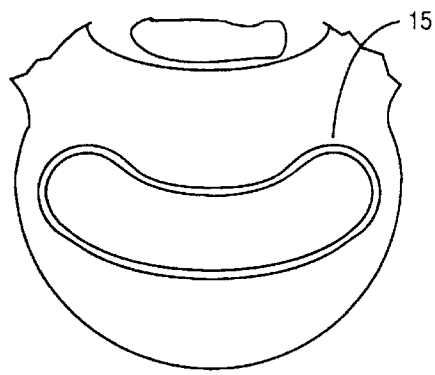
FIG. 6 is a top, simplified view of the banana-shaped cage of the invention in place upon the lumbar vertebrae of the human anatomy.
Figure 7:
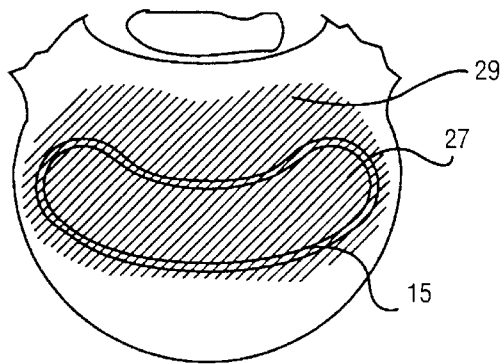
FIG. 7 is a similar view showing the placement of cancellous material within and anterior to the banana-shaped implant of the invention.
Figure 8:
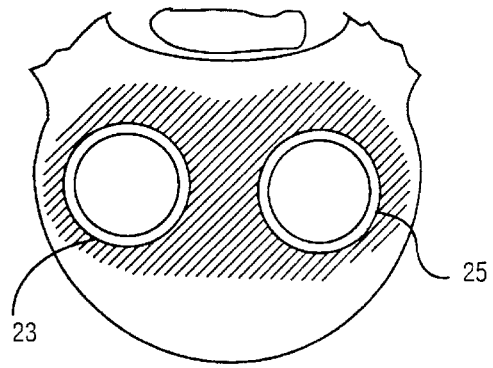
FIG. 8 shows the placement of prior art devices within the vertebral region.
Figure 10:
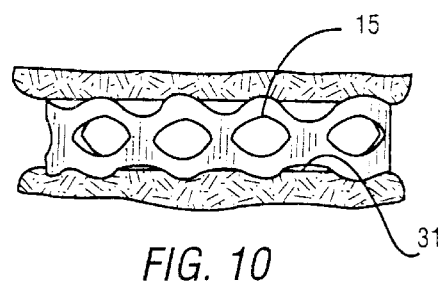
FIG. 10 is an isolated view of the intervertebral cage of the invention in place within the vertebral space.
Figure 9:
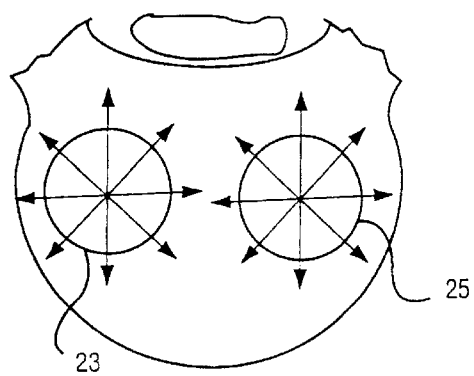
FIG. 9 illustrates the possible misalignment of the prior art devices in the vertebral space and schematically illustrating the possibility of asymmetric forces acting upon the device.
Figure 11:
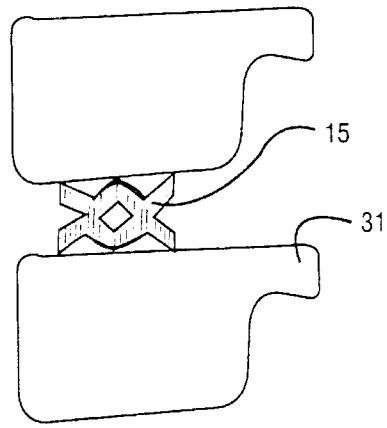
FIG. 11 is a simplified side view showing the placement of the cage of the invention within the vertebral space.

FIG. 5 shows a prior art pair of bone implants. In the discussion which follows, the advantages of the unitary cage of the invention will be apparent with respect to the prior art rings 23, 25. FIG. 6 shows the banana-shaped cage of the invention 15 within the disc space, as view from above. Note that the cage 15 is curved so that it mirrors the natural radius of curvature of the anterior and posterior curves of the vertebral bodies. FIG. 7 is merely intended to illustrate the placement of cancellous bone material 27, 29 both within the cage 15 and anterior thereto. FIG. 8 illustrates the proper placement of the prior art bone rings 23, 25, as viewed from above. FIG. 9 illustrates the possible misalignment of the prior art rings 23, 25 due to the two component nature of the procedure as well as the possibility of asymmetric forces acting upon the rings. FIG. 10 is an illustration of the cage prosthesis 15 of the invention inserted within the intervertebral disc space 31. FIG. 11 is a side view of the disc space 31 showing the proper placement of the cage of the invention.

Figure 12:
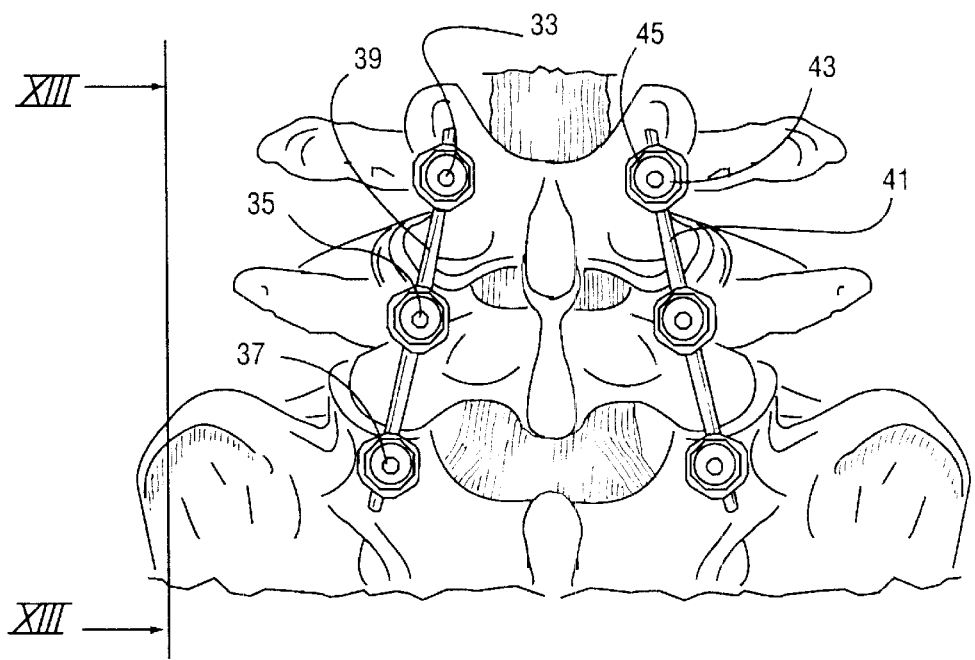
FIG. 12 is a posterior view of the human spinal column showing placement screws which are used during the discectomy process.
Figure 13:
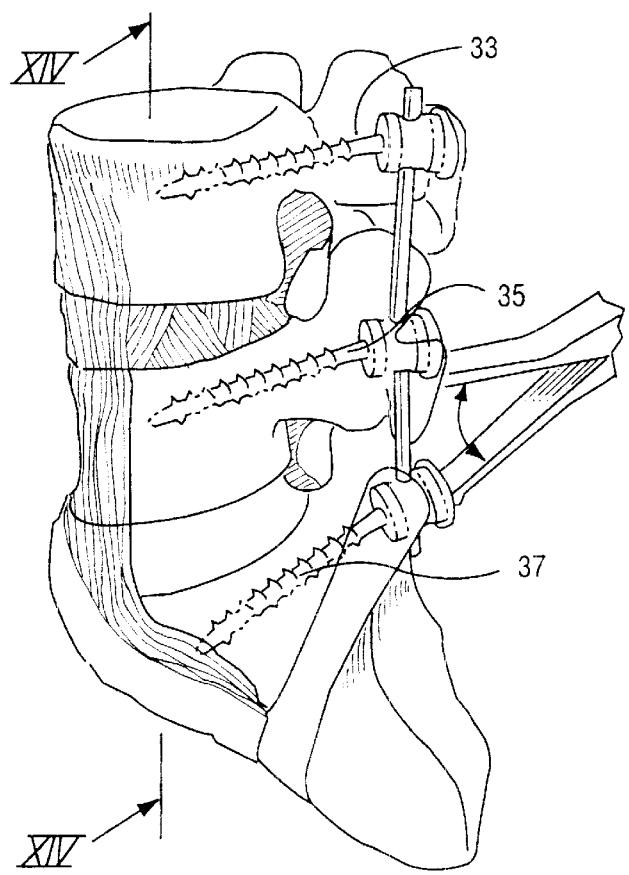
FIG. 13 is a side, partial perspective view of the human spinal column showing the use of an expansion tool to spread the L-4 and L-5 vertebrae.
Figure 14:
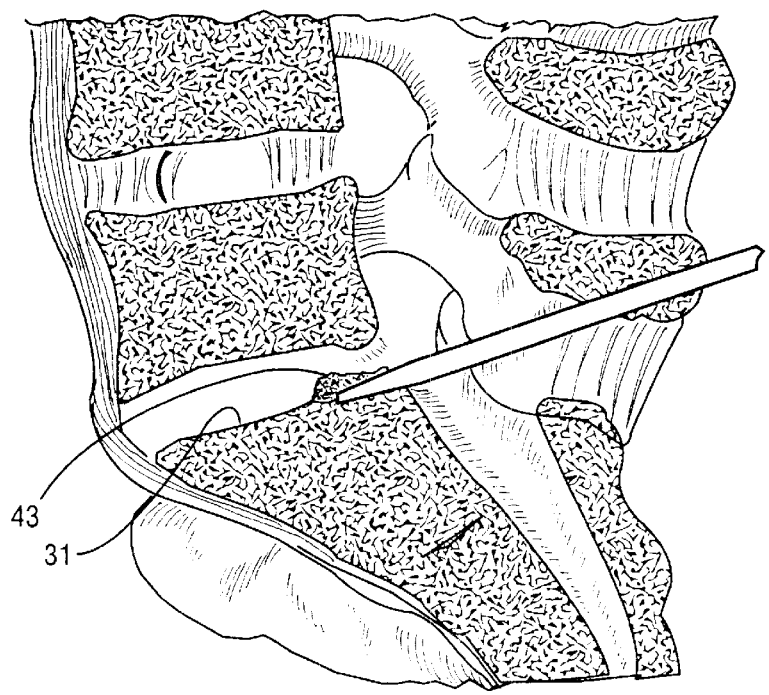
FIG. 14 is a side, partial cross-sectional view of the human spine, showing the removal of tissue to prepare the disc space for receiving the prosthesis of the invention.

The steps in a standard discectomy will be familiar to those skilled in the art. However, the steps will be briefly summarized below and with respect to FIGS. 12–17. In the case of a transforminal lumber interbody fusion and spondylosis thesis at L5 S1, the patient's left and right side are first detached parallel to the muscles in prone position. A wide exposure is carried out to the tips of the transverse processes. Resection of the facet joints L5 S1 on both sides is then performed. The pedicle is opened, as by means of an awl and the pedicle channel is probed. The pedicle is then tapped and screws are inserted. FIGS. 12 and 13 shows the screws 33, 35, 37 in place. The screws 33, 35, 37 in the L4, L5 and S1 positions are aligned by means of a head adjuster so that the screws are aligned in one plane. Rods 39, 41 are then placed (see FIG. 12). The rods 39, 41, in the particular procedure illustrated are fixed by means of inner screws 43 and outer nuts 45.

As illustrated schematically in FIG. 13, segmental distraction is then applied between S1 and L5 while a simultaneous posteriorly directed force at the cephalad end of the rod is carried out. The same procedure is then performed on the opposite side of the body. Resection and removal of the facet is the first step to achieve access to disk L5 S1 via the transforminal approach. This may be carried out with the use of a high speed bur or a pituitary ronjour. The medial portion of the facet joint can be resected by chisel and removed. Removal of the cephalad section of the S1 facet is accomplished, allowing enough space for the later placement of the implant prosthesis. Removal to the plane of the S1 pedicle but not into the pedicle may be carried out. By doing this, additional widening of the transforminal approach is established. Removable of the disk itself may be accomplished by means of straight and angled pituitary ronjours.

Proper resection of the postural lips of L5 S1 implants should be carried out. Additional spreading of the disk space is achieved by use of a wedge shaped impactor and specifically designed dilators. Further reduction of deformity is achieved by means of segmental distraction forces on both sides.

Disc space preparation is next carried out with the use of the cup curet with teeth (43 in FIG. 14) for cartilage removal and preservation of the implants. Further removal of any disk fragments is also carried out in this step of the procedure. Spongiosa and any additional morcilized graft can now be inserted to the anterior longitudinal ligament and anterior third of the disk space L5 S1. The spongiosa is condensed by the use of specially designed impactors.

Figure 15:
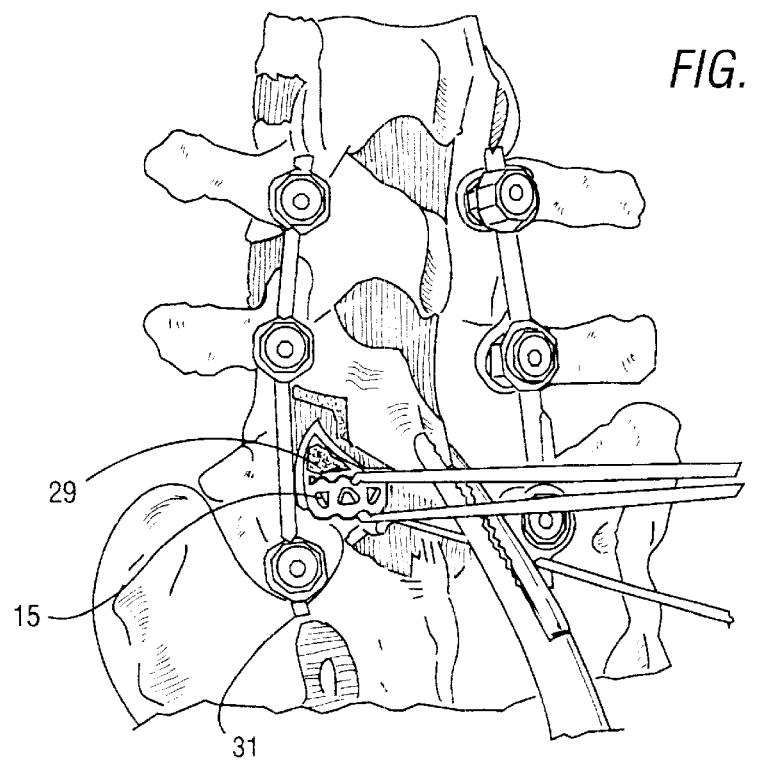
FIG. 15 is a posterior view of the spinal region showing the installation of the banana-shaped prosthesis of the invention.
Figure 16:
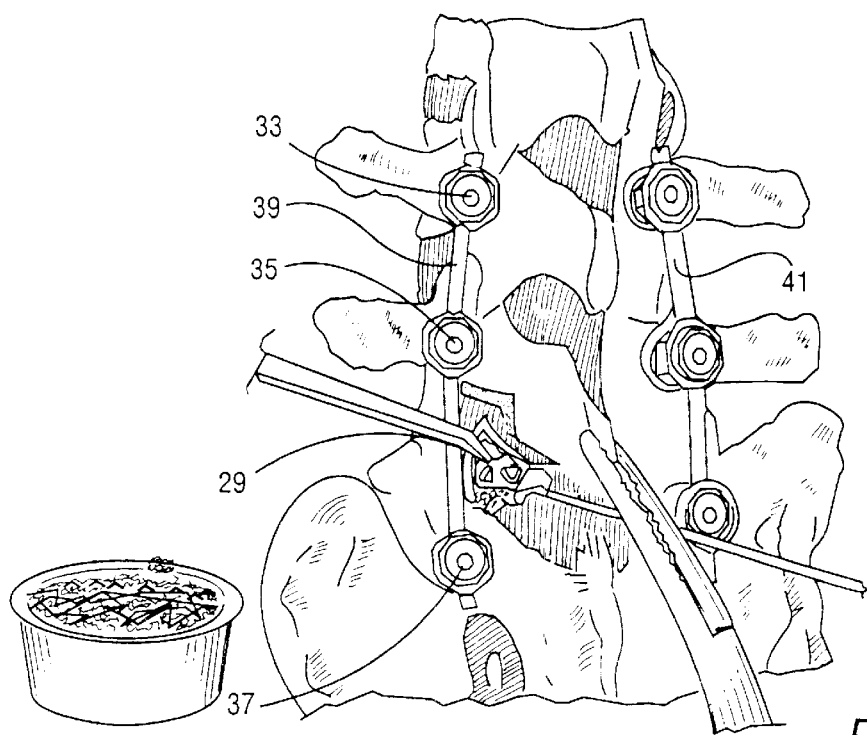
FIG. 16 is a view similar to FIG. 15 but showing the insertion of additional cancellous bone material within the disc space anterior to the cage implant.
Figure 17:
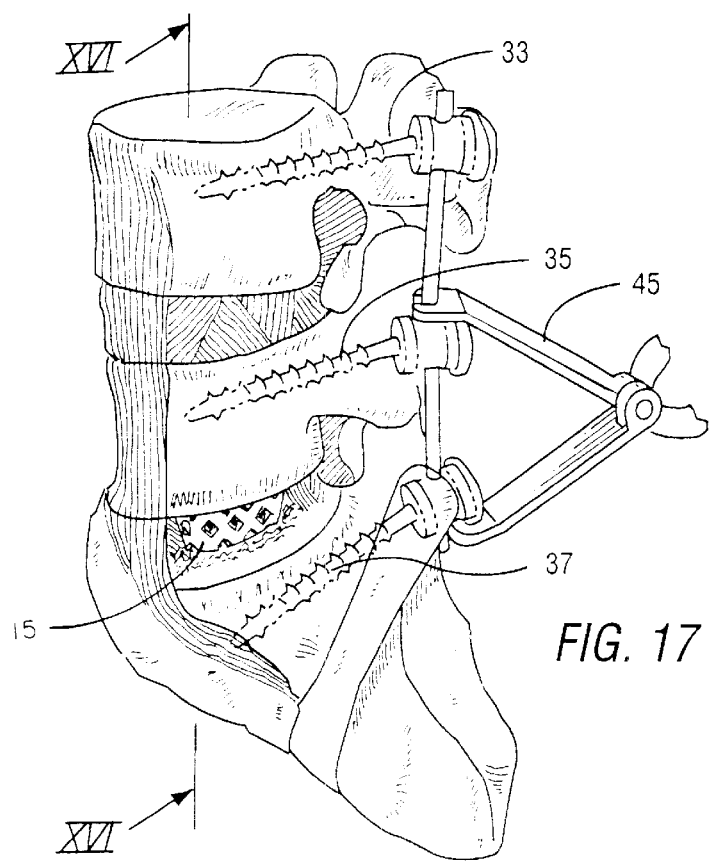
FIG. 17 is a view similar to FIG. 13 but showing the use of the compression tool to compress the installed prosthesis and associated vertebrae.

The properly sized cage implant of the invention can now be selected as determined by the height of the disk space after reduction. FIG. 15 illustrated the insertion of the banana-shaped cage 15 of the invention within the disc space 31, the cancellous bone material 29 also being visible. FIG. 16 shows the placement of additional cancellous bone material in the region surrounding the cage implant 15.

The nuts at L5 are now untightened. The conversion of the previously applied distractive forces are converted to compression forces by means of a compressor (45 in FIG. 17). This procedure is repeated alternatively on both sides. A final tightening sequence is then performed on the screws for rod-stabilization and maintenance of the desired correction. Additional application of bone for posterior lateral fusion may be accomplished as shown with respect to FIG. 16. The conversion of distraction forces to compression forces after positioning of the implant 15 allows restoration of both the tension band principle and load-sharing principle within the fused segment.

Figure 18:
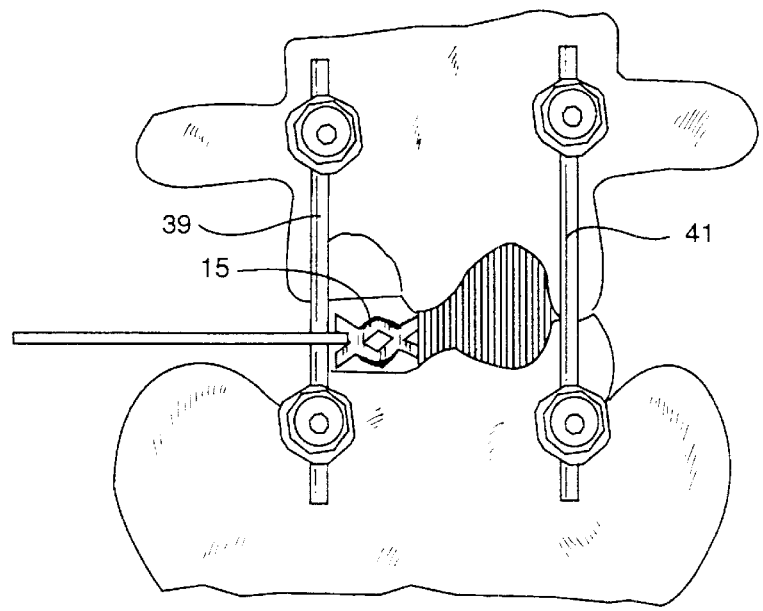
FIG. 18 is a simplified detail view of the insertion of the cage of the invention, illustrating the curved disc space and removed tissue.
Figure 19:
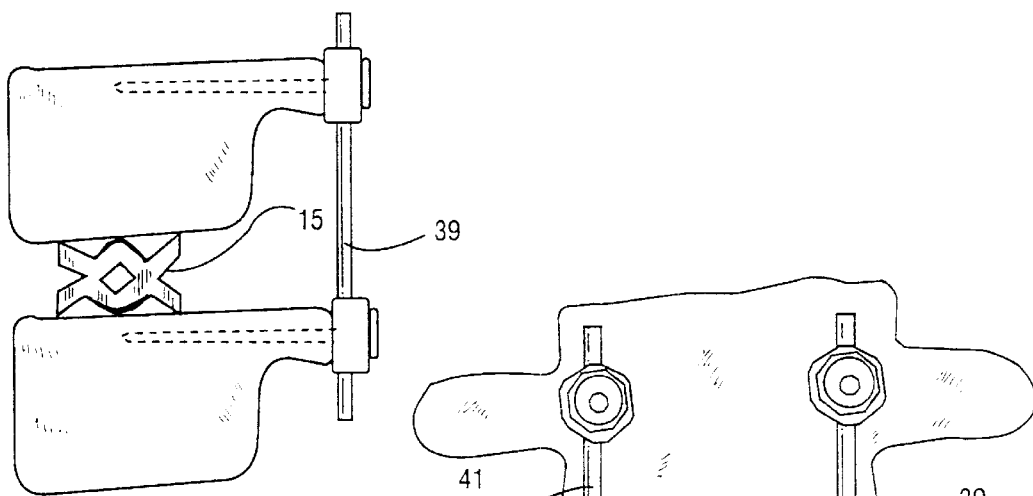
FIG. 19 is a detail side view illustrating the placement of the cage of the invention within the intervertebral space.
Figure 20:
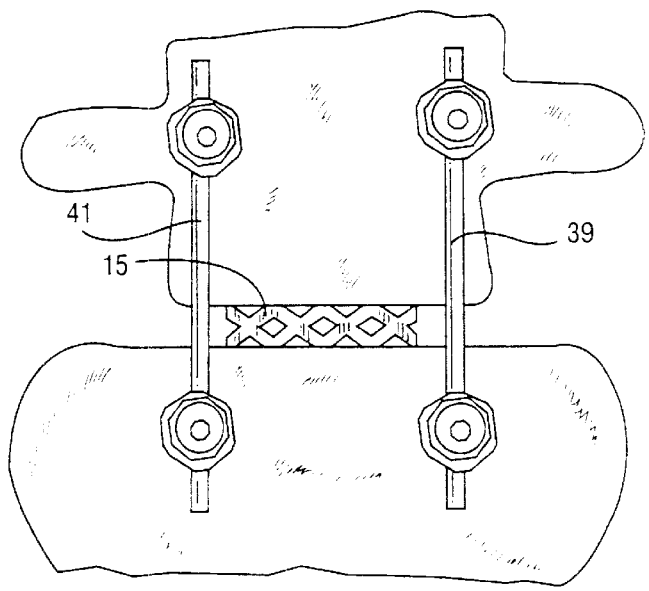
FIG. 20 is a back view showing the placement of the cage within the disc space.

FIG. 18 is an additional view of the insertion of the cage 15 of the invention within the disc space showing the curved nature of the disc space. FIGS. 19 and 20 are side and back views, respectively, of the properly placed cage.

An invention has been provided with several advantages. The unitary banana-shaped cage of the invention is easier and safer to place within the prepared disc space and is mechanically more stable than the previous two component systems currently in use. The curvature of the cage of the invention mirrors the natural curvature of the anterior and posterior curves of the vertebral bodies. It can be placed from either the anterior position or posterolateral position after standard discectomy. The implant of the invention can be manufactured from a variety of materials including both metals, metal alloys and synthetic, bioreabsorbable materials.

While the invention has been shown in only one of its forms, it is not thus limited but is susceptible to various changes and modifications without departing from the spirit thereof.

What is claimed is:

1. A transforaminal technique for providing vertebral inter-body fusion in the vertebral column of a human, the vertebral column being made up of a series of vertebral bodies each comprising a tri-joint complex which consists of an anterior disc with anterior and posterior curves and two posterior facet joints, the technique comprising the steps of:

preparing a space for receiving a unitary orthopedic prosthetic device between two vertebrae in a foraminal approach;

surgically inserting a unitary cage body into the space so created between the vertebrae, wherein the cage body is banana shaped as viewed from above, the body having an exterior surface and an interior surface, the interior surface defining an internal recess for receiving cancellous bone material during the implantation procedure and wherein the cage body has evenly spaced openings about a circumference of the body which form an interlinked mesh, the body also having upper and lower peripheral edges which form a sloping serpentine pattern, and wherein the body, when viewed from above, has a first radius of curvature of a front arc thereof and a second radius of curvature of a back arc thereof, the first radius of curvature and the second radius of curvature of the cage body mirroring a natural radius of curvature of the anterior and posterior curves of the anterior discs, the ratio of the first radius of curvature to the second radius of curvature being selected to allow insertion of the cage body between adjacent vertebrae in a transforaminal approach.

2. The technique of claim 1, wherein the cage body is selectively sized to fit within a vertebral disk space of a human anatomy allowing adequate space for additional cancellous bone anterior to the cage body within the disk space.

3. The technique of claim 2, wherein the cage body is formed of a hard metal alloy.

4. The technique of claim 3, wherein the cage body is formed of a titanium alloy.

5. A transforaminal technique for providing vertebral inter-body fusion in the vertebral column, the technique comprising the steps of:

preparing a space for receiving a unitary cage body between two vertebrae in a transforaminal approach, including the steps of;

(A) detaching the patient's left and right side parallel to the patient's muscles in prone position;

(B) opening the patient's pedicle and probing the channel thereof;

(C) tapping the patient's pedicle and inserting screws therein;

(D) placing rods through openings provided in the screws and fixing the rods by means of outer nuts;

(E) resecting a medial portion of the patient's facet joint; removing the medial portion, followed by removal of a cephalad section of the facet, allowing sufficient space for the later transforaminal placement of the cage body;

(F) removing the patient's disk;

(G) preparing a disc space by removing cartilage and removing of any disk fragments present in the space;

(H) inserting the cage into the disc space so prepared by a transforaminal approach into the prepared disc space;

(I) untightening the nuts on the rods, whereby the previously applied distractive forces are converted to compression forces; and wherein the cage body which is surgically inserted into the space so created between the vertebrae, wherein the cage body is banana shaped as viewed from above, the body having an exterior surface and an interior surface, the interior surface defining an internal recess for receiving cancellous bone material during the implantation procedure and wherein the cage body has evenly spaced opening about a circumference of the body which form an interlinked mesh, the body also having upper and lower peripheral edges which form a sloping serpentine pattern, and wherein the body, when viewed from above, has a first radius of curvature of a front arc thereof and a second radius of curvature of a back arc thereof, the ratio of the first radius of curvature to the second radius of curvature being selected to allow insertion of the cage body between adjacent vertebrae in a transforaminal approach.

* * * * *